United States Patent [19]

Unoguchi et al.

[11] 4,449,188

[45] May 15, 1984

[54] APPARATUS AND METHOD FOR CONTROLLING HUMIDITY

[75] Inventors: Takehiko Unoguchi, Kyoto; Seiro Hasegawa, Ikeda; Katsuyuki Fujito, Higashi-Osaka; Atsushi Nishino, Neyagawa; Akihiko Yoshida, Taishi-bashi, all of Japan

[73] Assignee: Matsushita Electrical Industrial Co., Tokyo, Japan

[21] Appl. No.: 318,552

[22] Filed: Nov. 5, 1981

Related U.S. Application Data

[63] Continuation of Ser. No. 128,877, Mar. 10, 1980, abandoned.

[30] Foreign Application Priority Data

Mar. 12, 1979 [JP] Japan .................................. 54-29151

[51] Int. Cl.$^3$ ........................ G06G 7/66; G05D 22/02
[52] U.S. Cl. .................................... 364/505; 165/21; 236/44 R; 307/118; 328/4; 340/602; 364/418
[58] Field of Search ............... 364/130, 183, 418, 505, 364/506, 556, 557; 361/286; 307/116, 118; 328/4; 324/61 R, 65 R; 340/602, 604; 236/44, 44 A, 44 C, 44 E; 73/336.5; 165/21

[56] References Cited

U.S. PATENT DOCUMENTS

| | | | |
|---|---|---|---|
| 3,547,348 | 12/1970 | Kruper | 236/44 |
| 3,689,907 | 9/1972 | Guajardo | 340/602 |
| 3,710,244 | 1/1973 | Rauchwerger | 361/286 X |
| 3,957,200 | 5/1976 | Young | 236/44 R |
| 4,092,635 | 5/1978 | Warner | 340/602 X |
| 4,156,268 | 5/1979 | Gallant | 361/286 |
| 4,161,660 | 7/1979 | Gallant | 328/4 X |

FOREIGN PATENT DOCUMENTS 1575167  9/1980  United Kingdom .

*Primary Examiner*—Joseph F. Ruggiero
*Attorney, Agent, or Firm*—Lowe, King, Price & Becker

[57] ABSTRACT

Apparatus for controlling humidity comprises a humidity sensing circuit including a humidity sensing element the electrostatic capacitance of which varies in accordance with the ambient relative humidity, and an air-conditioning system responsive to the sensed humidity. The humidity sensing element is charged and discharged repeatedly in accordance with a pulse train signal, and a period required for the voltage across the sensing element is measured during charging by a comparison between the voltage and a reference voltage. The pulse width or the reference voltage may be changed to select a desired reference humidity. A hysteresis characteristic may be given to render the operation of the circuit stable. When an SCR is controlled by the output signal of the humidity sensing circuit, the frequency of the pulse train signal is selected to be greater than four times the frequency of the voltage applied to the SCR.

18 Claims, 11 Drawing Figures

APPARATUS AND METHOD FOR CONTROLLING HUMIDITY

This is a continuation of application Ser. No. 128,877, filed Mar. 10, 1980 abandoned.

FIELD OF THE INVENTION

This invention generally relates to apparatus for controlling humidity which adjusts ambient humidity by means of a humidifier and/or a dehumidifier in accordance with the relative humidity sensed. More particularly, the present invention relates to apparatus for controlling humidity having a humidity sensing element the electrostatic capacitance of which varies in accordance with the ambient humidity.

BACKGROUND OF THE INVENTION

In a conventional apparatus for detecting the ambient humidity, hairs or specific chemical fibers are utilized for measuring the ambient humidity by using the expansion and contraction characteristics of these materials. However, the accuracy of the measured humidity by means of such materials is very low, and therefore, such humidity measuring means is not practical for precise control of the ambient humidity. Recently, a humidity sensing element the electrostatic capacitance of which varies in accordance with the ambient humidity, has been developed. When such a sensing element is utilized as a transducer, an electrical circuit which measures the capacitance of the sensing element is required to produce an electrical signal indicative of the capacitance and therefore the humidity. There are several possibilities for such an electrical circuit. For instance, an A.C. bridge or a resonant circuit may be used to measure the capacitance of the sensing element. However, when employing the above mentioned techniques, troublesome steps are required and furthermore, the electrical circuits for achieving the above mentioned techniques are too complex in construction.

Some of the inventors of the present invention had already proposed in a published British patent specification Ser. No. 2 017 924 A) a new humidity sensing element the electrostatic capacitance of which varies in accordance with the surrounding relative humidity and thus indicates the relative humidity. In addition, the inventors of the present invention had already prosed in another published British patent specification Ser. No. 2 020 434 A) an electrical circuit for displaying the realtive humidity measured by the sensing element of the above mentioned variable-capacitance type.

The above mentioned humidity sensing element is quick in response, and has a relatively high accuracy, while the element can be manufactured with low cost. When such a sensing element is used, it is preferable to measure the time required for the voltage across the sensing element which is charged by an electric current through a resistor, to rise 0.6 to 0.7 times the voltage of the power source applied to the charging circuit, in order to accurately measure the ambient humidity inasmuch as the equivalent series resistance and the dielectric loss angle of tan $\Gamma$ in the humidity sensing element are much greater that those in ordinary capacitive elements.

The inventors of the present invention have devised various improvements as to electrical circuits which measure the capacitance of the above mentioned humidity sensing element the electrostatical capacitance of which varies in accordance with the ambient relative humidity, and thus indicates the sensed humidity. These improvements, which will be described hereinbelow in detail, are significant when it is intended to apply such an electrical circuit to apparatus for controlling humidity or to apparatus which should be controlled in accordance with the sensed relative humidity.

It is, therefore, a primary object of the present invention to provide apparatus for controlling humidity in which the ambient relative humidity is accurately measured.

Another object of the present invention is to provide apparatus for controlling humidity with which the ambient relative humidity may be readily adjusted for a desired value.

A further object of the present invention is to provide apparatus for controlling humidity in which the ambient relaitve humidity is accurately measured irrespectively of the fluctuation in the power source voltage.

A still further object of the present invention is to provide apparatus for controlling humidity, the operation of which is hardly influenced by external noises.

A still further object of the present invention is to provide apparatus for controlling humidity, which is simple in construction and is low in cost.

In accordance with the present invention, there is provided apparatus for controlling humidity, including a humidity sensing circuit for producing an output signal indicative of the ambient relative humidity; and means for controlling the humidity in accordance with said output signal, said humidity sensing circuit comprising: (a) a humidity sensing element, the electrostatic capacitance of which varies in accordance with the ambient relative humidity; (b) a resistor connected in series with said humidity sensing element, said series circuit of said resistor and said humidity sensing element being connected to a D.C. power source so that said humidity sensing element is charged through said resistor; (c) a pulse generator for producing an output pulse train signal; (d) a switching circuit responsive to said pulse train signal for discharging charge prestored in said humidity sensing element; and (e) a voltage comparator responsive to the voltage across said humidity sensing element and to a reference voltage for producing an output signal which indicates that the humidity sensed has a predetermined relationship with respect to a reference humidity.

BRIEF DESCRIPTION OF THE DRAWINGS

These and other objects and features of the present invention will become more readily apparent from the following detailed description of the preferred embodiments taken in conjunction with the accompanying drawings in which.

DETAILED DESCRIPTION OF THE PREFERRED EMBODIMENTS

Figure 1:
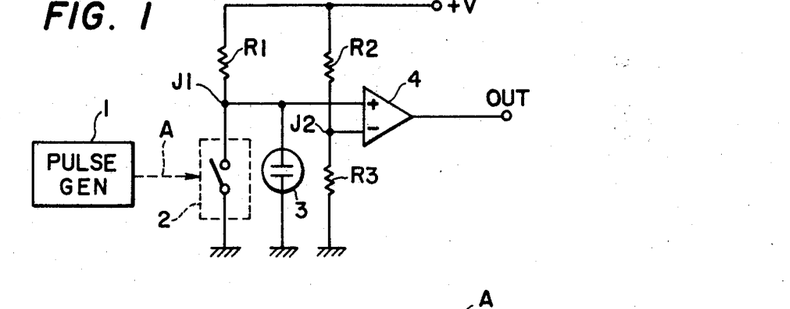
FIG. 1 is a schematic circuit diagram of an embodiment of a humidity sensing circuit included in the apparatus for conrolling the humidity according to the present invention.

Reference is now made to FIG. 1 which shows a first embodiment of the humidity sensing circuit included in the apparatus for controlling humidity according to the present invention. The humidity sensing circuit comprises a pulse generator 1, a switching circuit 2, a humidity sensing element 3, a voltage comparator 4, a resistor R1, and a voltage divider consisting of two resistors R2 and R3. The pulse generator 1 produces a train of pulses the width of which is adjustable. The pulse generator 1 has an output terminal connected to the switching circuit 2 so that the pulse signal produced by the pulse generator 1 is used to control the ON-OFF state of the switching circuit 2. Although the switching circuit 2 is illustrated by a symbol of a mechanical switch or relay, the switching circuit may be a semiconductor switch such as a transistor. The switching circuit 2 and the resistor R1 are connected in series; and this series circuit is interposed between a power source $+V$ and ground. The humidity sensing element 3 functions as a capacitor where the capacitance thereof varies in accordance with the ambient relative humidity. A detailed description of the humidity sensing element is given in the aforementioned two British patent specifications, and therefore, further description of the humidity sensing element is omitted. The humidity sensing element 3 is connected in parallel with the switching circuit 2. A junction J1 connecting the resistor R1, the switching circuit 2 and the humidity sensing element 3 is connected to a noninverting input terminal (+) of the comparator 4, which has an inverting input terminal (−) and an output terminal. The resistors R2 and R3 are connected in series at a junction J2; and this series circuit is interposed between the power source $+V$ and ground. The second mentioned junction J2 is connected to the inverting input terminal (−) of the comparator 4.

Figure 2:
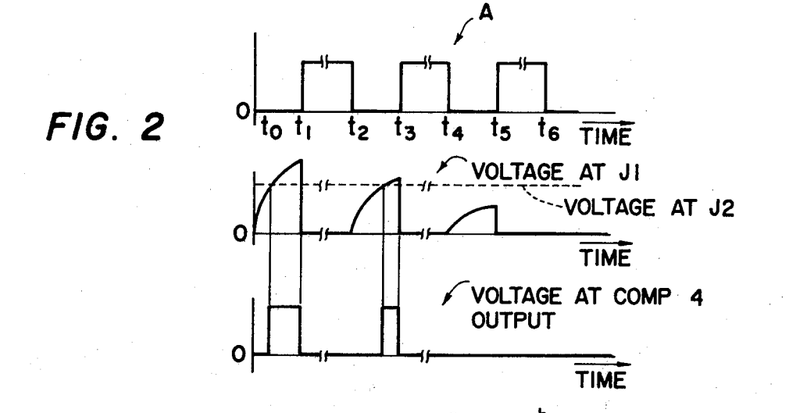
FIG. 2 is a waveform diagram useful for understanding the operation of the circuitry of FIG. 1.

The humidity sensing circuit of FIG. 1 operates as follows: FIG. 2 is a waveform diagram showing voltages at various points in the circuit of FIG. 1; and the pulse generator 1 produces a pulse train signal "A" as is shown in the waveform diagram. It is assumed that the switching circuit 2 assumes its ON state while the output voltage of the pulse generator 1 is of high level. Therefore, when the output voltage of the pulse generator 1 drops to its low level at time $t_0$, the switching circuit 2 opens, i.e. turns off, so that the humidity sensing element 3 starts being charged by an electric current applied via the resistor R1. The second waveform indicates the voltage variation at the first junction J1, namely, the voltage across the humidity sensing element 3. As is clearly shown, the voltage at the first junction J1 exponentially rises from $t_0$. The dotted line in the second waveform of FIG. 2 indicates a reference voltage obtained by the voltage divider including the resistors R2 and R3. This reference voltage at the second junction J2 is fixed and is constant. When the voltage at the first junction J1 equals or exceeds the reference voltage at the second junction J2, the voltage comparator 4 produces an output signal of high level as shown in the third waveform of FIG. 2.

At time $t_1$ the output voltage of the pulse generator 1 rises and thus the switching circuit 2 closes its contacts causing the charges prestored in the humidity sensing element 3 to discharge through the switching circuit 2. As a result the voltage at the first junction J1 drops to zero so that the output voltage of the voltage comparator 4 turns to low level. Since the discharge is effected instantaneously, the output voltage of the comparator 4 is inverted from high level to low level at substantially time $t_1$.

In the above, it has been assumed that the capacitance of the humidity sensing element 3 is relatively rapidly charged. However, the capacitance of the humidity sensing element 3 varies as the ambient relative humidity rises or drops. Namely, the time constant defined by the resistance of the resistor R1 and the capacitance of the humidity sensing element 3 changes as the ambient relative humidity changes so that the charging time of the humidity sensor 3 varies accordingly. In other words, the slope of the exponential curve indicating the voltage variation across the humidity sensing element 3 is directly related to the ambient relative humidity.

In the following period defined by time $t_2$ and $t_3$, it is assumed that the capacitance of the humidity sensing element 3 has been increased compared with before. Since the capacitance of the humidity sensing element 3 is greater than before, the time constant of the charging circuit, i.e. the series circuit of the resistor R1 and the humidity sensing element 3, is greater than before and thus it takes more time for the voltage at the first junction J1 to reach the reference voltage. Accordingly, the pulse width of the output signal of the comparator 4 is narrower than before. The charge stored in the humidity sensing element 3 is discharged at time $t_3$ in the same manner as described in the above.

Let us suppose that the capacitance of the humidity sensing element 3 is further increased due to the change in the ambient humidity. The exponential curve between time $t_4$ and $t_5$ corresponds to this state. Namely, in this period between $t_4$ and $t_5$ the voltage across the humidity sensing element 3 cannot reach the reference voltage since the time constant of the charging circuit is so large. As a result, the output voltage of the comparator 4 is maintained at its low level.

From the above, it will be understood that the output voltage of the comparator 4 indicates whether the sensed ambient relative humidity is above or below a predetermined value. This predetermined relative humidity may be set by adjusting either the pulse width of the pulse train signal from the pulse generator 1 or the dividing ratio in the voltage divider since the following relationship has to be satisfied:

$$T > -C_{RH} \cdot R1 \cdot l_n\left(1 - \frac{R3}{R2 + R3}\right)$$

wherein
T is the period for which the switching circuit 2 assumes its OFF state (namely, the charging period);
$C_{RH}$ is the capacitance of the humidity sensing element; and
R1, R2 and R3 are the resistances of the resistors R1, R2 and R3.

In this way, a suitable reference humidity may be readily set so that when the humidity sensing circuit of FIG. 1 is adapted to a humidity controlling apparatus or system, the ambinent relative humidity may be easily adjusted to a desired value.

Figure 3:
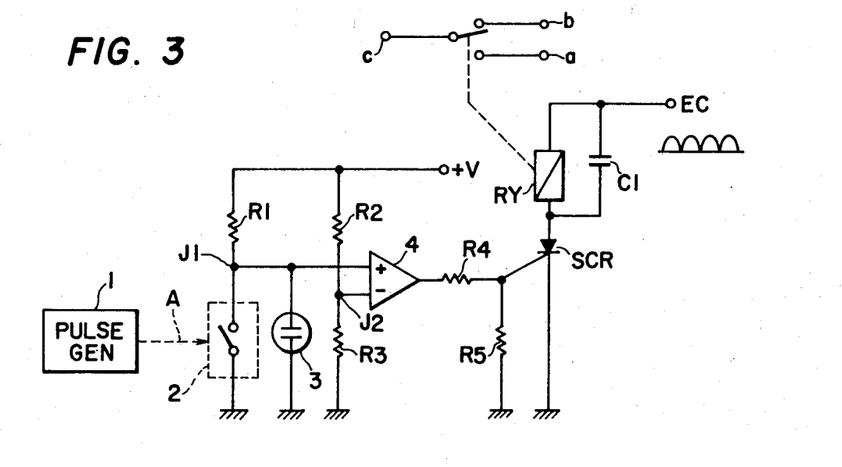
FIG. 3 is a schematic circuit diagram of an embodiment of the apparatus for controlling the humidity according to the present invention, which apparatus includes the circuitry of FIG. 1.

FIG. 3 is a circuit diagram of the apparatus for controlling humidity according to the present invention, and the circuit of FIG. 3 includes the humidity detecting circuit of FIG. 1. The same circuits and elements as in FIG. 1 are designated by like numerals. The output terminal of the voltage comparator 4 is connected to an input terminal of a humidity controlling circuit which comprises resistors R4 and R5, an SCR (silicone controlled rectifier), a relay RY, and a capacitor C1. In detail, the output terminal of the comparator 4 is connected via the resistor R4 to a gate electrode of the SCR, the cathode electrode of which is connected to ground. The winding shown in the form of a black box, of the relay RY and the capacitor C1 are connected in parallel and this parallel circuit is interposed between a power source Ec and the anode electrode of the SCR. The relay RY has a movable contact (no numeral) connected to a terminal "c" and first and second stationary contacts (no numeral) respectively connected to terminals "a" and "b". The movable contact of the relay RY is arranged to be in contact with the first stationary contact when the relay winding is energized. The contacts "a", "b" and "c" may be connected to a power circuit of a humidifier and/or a denumidifier when it is intended to control the ambient relative humidity. Furthermore, these contacts "a", "b" and "c" may be connected to a power circuit of a device or apparatus the operation of which is to be controlled in accordance with the sensed humidity. For instance, a cooking appliance, such as a microwave range may be switched off when the humidity inside the microwave range rises above a predetermined humidity.

The operation of the apparatus of FIG. 3 will be described hereinbelow in connection with a case that a humidifier (not shown) is controlled by the circuitry of FIG. 3. As described before in connection with the operation of the circuitry of FIG. 1, a desired relative humidity may be set by adjusting the width of the each pulse from the pulse generator 1. If the sensed ambient relative humidity is below this preset humidity, the voltage comparator 4 produces an output pulse signal. This pulse signal from the comparator 4 is applied via the resistor R4 to the gate electrode of the SCR to trigger the same. As a result, the SCR turns conductive allowing an electric current to flow through the winding of the relay RY. Accordingly, the movable contact of the relay RY is atracted to be in contact with the first stationary contact. Namely, the terminals "a" and "c" are electrically connected to each other to energize the humidifier.

The humdifier starts operating and thus the ambient relative humididty rises as time goes. When the ambient relative humididty exceeds the preset humidity defined by the pulse width from the pulse generator 1, no output pulse signal appears at the output terminal of the comparator 4 (see the period between $t_4$ and $t_5$ in the waveform diagram of FIG. 2). In the absence of the pulse which is used as a trigger pulse for the SCR, the SCR turns nonconductive interrupting the current through the winding of the relay RY. Consequently, the relay RY is deenergized and thus the movable contact returns to its original position by a force of a spring (not shown) to be in contact with the second stationary contact. As the circuit between the terminals "a" and "c" opens, the humidifier is deactivated.

In order that the circuitry of FIG. 3 operates in the above mentioned manner, the electric current supplied from the power source Ec has to satisfy the following requirement. Namely, the electric current from the power source Ec includes ripple components such that the voltage repeatedly equals zero volt. For instance, therefore, the current applied to the relay RY may be obtained by half-wave or full-wave rectifying a regular commercial A.C. power source. In FIG. 3, a full-wave rectified voltage is illustrated for convenience.

The capacitor C1 connected across the winding of the relay RY is employed for preventing the movable contact thereof from chattering or vibrating. The resistor R5 connected between the gate and cathode electrodes of the SCR is a bias resistance for making the operation of the SCR stable.

Generally speaking, the frequency of the commercial A.C. voltage is between 50 and 60 Hz, and therefore, the frequency of the trigger pulses to be applied to the gate electrode of the SCR should be theoretically above the twice the frequency of the A.C. voltage. Namely, the trigger pulses have to be produced with a frequency of above 100 to 120 Hz. However, since the commercial power source is of a sinusoidal wave, the voltage applied to the SCR via the relay RY is not necessarily above a sufficient level for rendering the SCR conductive at an instant that the trigger pulse is applied to the gate electrode of the SCR. For this reason in order that the circuitry of FIG. 3 operates in a stable manner, it is preferable that the frequency of the trigger pulses is over four times the frequency of the sinusoidal A.C. voltage from which the current having ripple components is produced. In the embodiment of FIG. 3, the capacitance of the humidity sensing element 3 varies centering around $1 \times 10^{-7}$ F so that by selecting the resitance of the resistor R1 between 10 and 15 Kohms and by setting the voltage dividing ratio by the resistors R2 and R3 to approximately 0.6, the circuitry is capable of functioning in a practical level.

Figure 4:
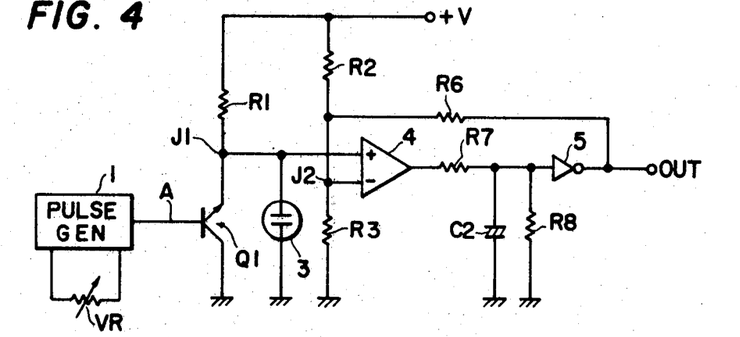
FIG. 4 is a schematic circuit diagram of another embodiment of the humidity sensing circuit to which a hysteresis characteristic is given.

Reference is now made to FIG. 4 which shows a detailed example of a humidity sensing circuit included in the apparatus for controlling humidity according to the present invention. In the circuitry of FIG. 4, the same elements and circuits as used in the previous embodiments are designated by like numerals. The pulse generator 1 is equipped with a variable resistor VR so that the time constant in the pulse generator 1 is readily adjusted manually by manipulating the variable resistor VR. Namely, the pulse width of the pulse train signal may be set to a desired value and thus the charging period for the humidity sensing element 3 may be set at will.

A transistor Q1 is used in place of the switching circuit 2 of FIG. 1 and FIG. 3 so that the collector-emitter path of the transistor Q1 will be conductive in response to a bias voltage from the pulse generator 1 to the base electrode of the transistor Q1.

Although in the embodiment of FIG. 3, the output terminal of the voltage comparator 4 is connected through only the resistor R4 to the gate electrode of the SCR, in the embodiment of FIG. 4, a hysteresis circuit is interposed between the second junction J2 and an output terminal OUT of the entire circuitry of FIG. 4. The hysteresis circuit comprises a resistor R6, while a voltage-hold circuit including a resistor R7 and a capacitor C2 follows the comparator 4. The resistor R7 is connected between the output terminal of the comparator 4 and an input terminal of an inverter 5. The capacitor C2 and a resistor R8 are connected in parallel and this parallel circuit is connected between the input terminal of the inverter 5 and ground. The output terminal of the inverter 5 is connected to the output terminal OUT, and is further connected via the resistor R6 to the inverting input terminal (−) of the comparator 4. The capacitor C2 and the resistor R7 constitute a voltage-hold circuit and thus the output pulse from the comparator 4 is temporarily stored in the capacitor C2.

The inverter 5 is constructed of a circuit having a high input impedance; for example, a C-MOS type integrated circuit may be used. The output voltage of the inverter 5 reverses as the voltage across the capacitor C2 exceeds a threshold of the inverter 5. A portion of the inverted output voltage is fed back via the resistor R6 to the voltage divider, which supplies the comparator 4 with the reference voltage, for obtaining a hysteresis characteristic.

Figure 5:
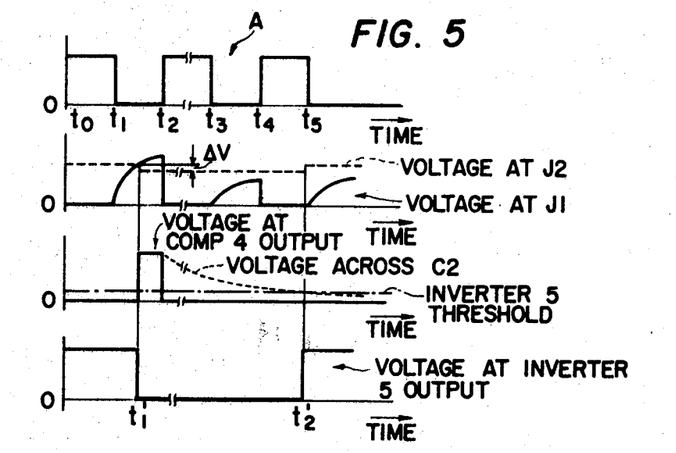
FIG. 5 is a waveform diagram useful for understanding the operation of the circuitry of FIG. 4.

The operation of the circuitry of FIG. 4 will be further descirbed in detail with reference to a waveform diagram of FIG. 5. The voltage at the base of the transistor Q1 varies between high and low levels in accordance with the pulse width. As is shown in the first waveform in FIG. 5, during a period between $t_0$ and $t_1$ the voltage at the base is high so that the transistor Q1 is conductive for this period. The emitter and collector electrodes of the transistor Q1 are connected in the reverse direction with respect to regular connection for making the saturation voltage $V_{CE(SAT)}$ thereof low. Since the collector-emitter path is conductive during this period between $t_0$ and $t_1$, the voltage at the emitter, namely the voltage at the first junction J1 connecting the charging resistor R1 and the humidity sensing element 3, is substantially zero.

In the following period defined by $t_1$ and $t_2$, the voltage at the base electrode of the transistor Q1 is of low level so that the transistor Q1 becomes nonconductive allowing an electric current to flow into the humidity sensing element 3. In other words, the humidity sensing element 3 is charged after time $t_1$. The duration required for fully charging the humidity sensing element 3 is in proportion to the capacitance of the same, which capacitance varies in accordance with the ambient relative humidity. If the period of time required for the voltage at the first junction J1 to reach the reference voltage at the second junction J2 is less than the period of time between $t_1$ and $t_2$, the comparator 4 produces an output pulse signal as is shown in the third waveform. In other words, when the sensed humidity is below a predetermined value set by the pulse width, the comparator 4 produces an output pulse signal. Since the comparator 4 produces an output pulse whenever the voltage at the non-inverting input terminal (+) is above the voltage at the inverting input terminal (−), pulses are produced repeatedly as long as the sensed humidity is below the preset value. Such repeated pulses, however, are not suitable for controlling a humidifier and/or a dehumidifier for such apparatus for moistening and/or drying the air might repeat ON-OFF operation.

Therefore, in the embodiment of FIG. 4, the aforementioned voltage-hold circuit consisting of the resistor R7 and the capacitor C2 is utilized. Namely the voltage-hold circuit maintains the voltage across the capacitor C2 after the pulse from the comparator 4 disapears till a next pulse is applied to the voltage-hold circuit. A dotted exponential curve in the third waveform shows the voltage variation across the capacitor C2. As illustrated by the above mentioned dotted exponential curve, the charge prestored in the capacitor C2 gradually discharges through the resistor R8 so that the voltage across the capacitor C2 does not drop rapidly. The capacitor C2 and the resistor R8, therefore, constitute a discharging circuit and the time constant of the discharging circuit has to be determined such that the voltage across the capacitor C2 is maintained above a predetermined value until the following pulse is applied to the voltage-hold circuit. This predetermined value equals the threshold of the inverter 5. Accordingly, the inverter 5, which has been producing a low level output after time $t_1'$ in response to the high level output signal from the comparator 4, keeps its low level output signal as long as the voltage across the capacitor C2 is above the threshold which is shown in the third waveform in the form of a dot-dash line. During this period that the inverter 5 delivers a low level output voltage, this low level voltage is fed back via the resistor R6 to the second junction J2 lowering the reference voltage applied to the inverting input terminal (−) of the comparator 4. This means that the reference voltage at the inverting input terminal (−) is lowered by $\Delta V$ as shown in the second waveform of FIG. 5. As a result, a hysteresis characteristic is given to the comparator 4 so that undesirable hunting phenomena are avoided. Accordingly, the output signal at the output terminal OUT does not cause the following humidifier and/or dehumidfier to chatter. Turning back to the operation of the comparator 4, the comparator is so constructed to supply its output terminal with an electric current from a power source when the voltage at the noninverting input terminal (+) is higher than that at the inverting input terminal (−), and the output terminal of the comparator 4 will be open when the voltage at the non-inverting input terminal (+) is lower than that at the inverting input terminal (−).

After time $t_2$ the voltage at the base electrode of the transistor Q1 is high and thus the transistor Q1 is conductive discharging the charge prestored in the humidity sensing element 3. This discharge is done instantaneously so that the the voltage across the humidity sensing element 3, which voltage has been exponentially rising, suddenly drops to zero volt. As a result, the output voltage of the comparator 4 also drops to zero at time $t_2$. However, as described in the above, because of the voltage-hold circuit which follows the comparator 4 the voltage at the input terminal of the inverter 5 does not quickly drop for maintaining the low output voltage at the output terminal of the inverter 5. Therefore, the period of the pulses from the pulse generator 1 should be shorter than the time constant of the voltage-hold circuit.

Let us suppose that the ambient relative humidity rises as the humidifier has been activated, and therefore, the capacitance of the humidity sensing element 3 has been increased in a following period defined by $t_3$ and $t_4$. In this situation, the voltage at the first junction J1 cannot rise above the voltage at the second junction J2 for the time constant for charging the humidity sensing element is now greater than before. Consequently, the comparator 4 is not influenced at all by the variation in the voltage across the humidity sensing element 3 and thus the comparator 4 keeps producing a low level output as before. Therefore, the charge prestored in the capacitor C2 keeps discharging through the resistor R8 so that the voltage across the capacitor C2 approaches the threshold of the inverter 5. At time $t_2'$ the voltage across the capacitor C2 falls below the threshold voltage so that the output voltage at the inverter 5 turns high at $t_2'$. The high voltage at the output terminal of the inverter 5 is fed back via the resistor R6 to the second junction J2 regaining the original reference voltage.

Summarizing the above described operation with respect to hysteresis characterisitc, the output signal of the inverter 5 is changed when the sensed relative humidity drops below a preset humidity; and the output signal of the inverter 5 is changed when the sensed relative humidity exceeds a humidity a little higher than the preset humidity. Such a hysterisis characteristic is essential for operating a humidifier and/or a dehumidifier in a stable manner. If such a hysterisis characteristic were not given to apparatus for controlling a humidifier and/or dehumidifier, rapid cycling of ON-OFF operation, which is called hunting phenomena, would occur. Rapid cycling of ON-OFF operation is extremely disadvantageous in view of the life of the humidifier and/or dehumidifier and also the electricity consumption. In addition, hysterisis characteristic is significant since the humidifier and/or dehumidifier is not erroneously activated or deactivated by external noises.

Figure 6:
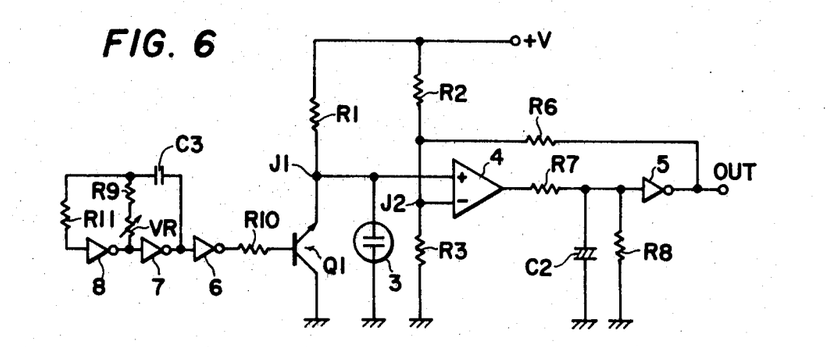
FIG. 6 is a schematic circuit diagram of another embodiment of the humidity sensing circuit in which pulse width is manually controlled for setting a reference humidity.
Figure 7:
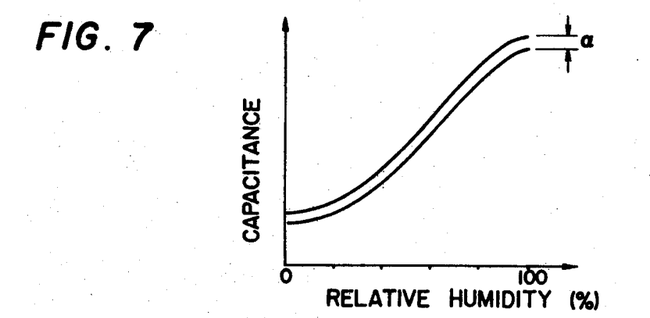
FIG. 7 and FIG. 9 are graphical representations showing variations in capacitance with respect to humidity throughout a given number of products of humidity sensing elements of first and second groups.
Figure 9:
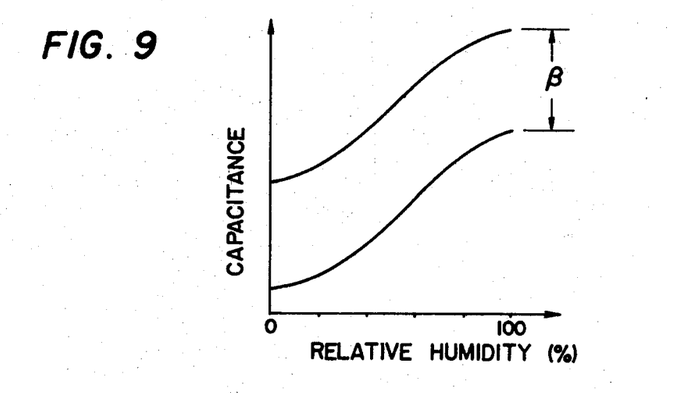

FIG. 6 shows a circuit diagram of another embodiment which is based on the circuitry of FIG. 4. The circuitry of FIG. 6 is substantially the same as that of FIG. 4 except that the detailed circuit diagram of the pulse generator 1 is illustrated. This embodiment of FIG. 6 features that a reference humidity may be manually set by means of a variable resistor VR included in the pulse generator 1. Namely, a desired humidity may be selected and this reference humidity may be continuously changed by waatching a linear scale associated with the nob of the variable resistor VR. This embodiment of FIG. 6 is suitable when the humidity sensing element 3 has its characteristic which falls between two curves shown in FIG. 7. FIG. 7 shows variations in the capacitance with respect to the relative humidity throughout a given number of sensing elements. Namely, the horizontal axis in the graph of FIG. 7 indicates the humdities, while the vertical axis indicates the capacitances; and a reference $\alpha$ corresponds to the maximum variation. FIG. 9 shows the variations with respect to another group of humidity sensing elements, and the maximum variation throughout a given number of products is designated as $\beta$. From the comparison between FIG. 7 and FIG. 9, it will be recognized that the variation in the first group of products of humidity sensing elements of FIG. 7 is much smaller than that of the second group.

Therefore, if a humdidity sensing element is selected from the above mentioned first group, having negligibly small variations, the variations throughout a number of products is not necessarily considered, and thus the aforementioned period of time T is readily obtained from the aforementioned formula if the resistances of the resistors R1 to R3 are set.

Turning back to FIG. 6, the pulse generator 1 comprises three inverters 6, 7 and 8, resistors R9, R10 and R11, and a capacitor c3 as well as the above mentioned variable resistor VR. These inverters 6, 7 and 8 are connected in series and an output terminal of the last inverter 6 in the series circuit is connected via the resistor R10 to the base electrode of the transistor Q1. The resistor R11 and the capacitor C3 are connected in series and this series circuit is connected between an input terminal of the first inverter 8 and an output terminal of the second inverter 7. The remaining resistor R9 and the variable resistor VR are connected in series and this series circuit is connected between an output terminal of the the first inverter 8 and a junction connecting the above mentioned resistor R11 and capacitor C3. Two inverters 7 and 8 among these three constitute a general square-wave generator together with the resistors R9 and R11, the variable resistor VR and the capacitor C3, while the remaining inverter 6 functions as a buffer circuit.

The above mentioned period T will be simply determined by the resistances of the variable resistor VR and the resistor R9, and the capacitance of the capacitor C3. Namely, by selecting the resistance of the resistor R9 and the capacitance of the capacitor C3 so as to obtain a suitable period T in view of the characteristic of the humidity sensing element 3, a circuit for controlling humidity, having relatively high accuracy and simple construction is easily obtained.

Figure 8:
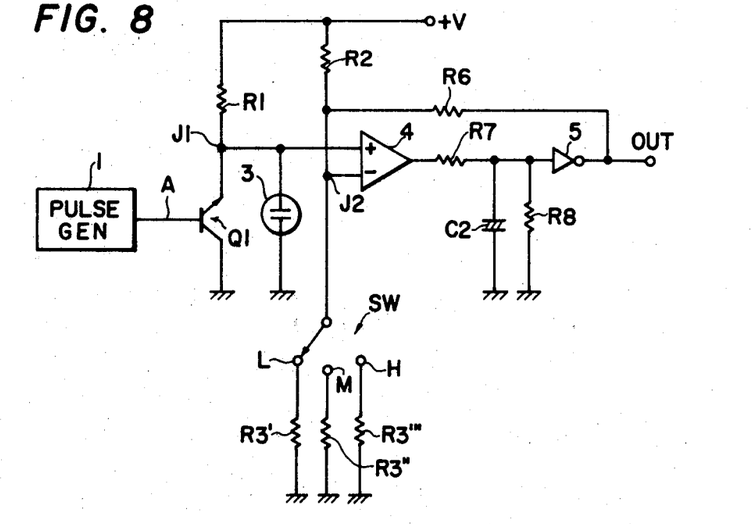
FIG. 8 is a schematic circuit diagram of another embodiment of the humidity sensing circuit in which the reference voltage for the comparator is manually changed for setting a reference humidity.

FIG. 8 is a circuit diagram of another embodiment also similar to that of FIG. 4. This embodiment is suitable when the humidity sensing element 3 is selected from the above mentioned second group having variations represented by FIG. 9. In accordance with the embodiment of FIG. 9 the reference humidity may be set stepwisely by means of a switch SW, such as a rotary switch. In detail, the number of steps with respect to the reference humidity is three, namely low humidity L, medium humidity M and high humidity H. This embodiment may be easily adapted to an air-conditioning system for household use since the number of elements constituting the entire circuitry is relatively small and therefore, the circuitry can be manufactured with low cost. A distinctive feature in this embodiment of FIG. 8 is that the circuitry operates in a practical level even though the humidity sensing element 3 is selected from a group of products, such as the second group of FIG. 9, having relatively large variations in its characteristics. Furthermore, although the particular characteristic of the humidity sensing element 3 is not known, such a humidity sensing element may be used if its approximate variation is ascertained.

In the embodiment of FIG. 8, three resistors R3', R3", and R3''' are substituted for the resistor R3 in FIG. 4; and one of these three resistors R3', R3" and R3''' is selectively connected to the second junction J2 by way of the above mentioned switch SW. This arrangement of stepwisely changing the resistance of the voltage divider is advantageous compared with other possibilities, such as changing the resistance of the resistor R1 or changing the resistance of the variable resistor VR in FIG. 6 for the following reasons. Namely, if the resistance of the resistor R1 is set extremely small, the electric current from the D.C. power source +V would be increased undesirably and the conductive resistance of the transistor Q1 would be increased. In addition if the resistance of the variable resistor VR is increased or decreased, the operation of the inverters 6, 7 and 8 in FIG. 6 would be likely unstable.

With the arrangement of FIG. 8, the above mentioned undesirable influences are prevented, while the aforementioned period T may be varies throughout a wide range so as to compensate for the variation in the characteristic of the humidity sensing element 3. The resistance of the resistors R3', R3" and R3"' are respectively determined in the following manner.

First of all, the humidity sensing element 3 is placed in a constant-humidity chamber (not shown), and the relative humidity in the constant-humidity chamber is set to a given value which corresponds to the preset low humidity L, such as 30% RH. The switch SW is then manipulated to select the position L to connect the resistor R3' to the second junction J2. The constant humidity in the chamber is sensed under this condition and then the resistance of the resistor R3' may be selected such that the reference voltage at the inverting input terminal (−) of the comparator 4 equals a critical value with which the output signal at the output terminal of the comparator 4 turns from high to low and vice versa.

After the resistance of the resistor R3' is determined, the resistances of the resistors R3" and R3"' are respectively determined in the same manner by setting the relative humidity in the constant-humidity chamber to the predetermined medium humidity, such as 50% RH, and then to the high humidity, such as 80% RH, while the switch SW is manipulated to select the positions M and H respectively.

From the above it will be clear that the characteristic of the circuitry may be readily matched with that of the humidity sensing element 3 without obtaining the characteristic data of the sensing element 3. Since the circuitry per se can be matched with the characteristic of the humidity sensing element 3, the charging voltage for the sensing element 3 does not have to be in a range between 0.6 and 0.7 times the voltage of the power source for performing humidity measurement with high accuracy. Therefore, when the circuitry of FIG. 8 is is adopted, there is no need to select humidity sensing elements having a predetermined characteristic from a number of products thereof. Accordingly, the yield in manufacturing the humidity sensing elements can be high, and most of the products can be utilized.

According to the embodiment of FIG. 8 the voltage difference, i.e. ΔV, at the second junction J2 obtained as the result of the aforementioned characteristic changes as the switch SW is manipuated since the voltage dividing ratio changes accordingly. In other words, the hysteresis range in the FIG. 8 arrangement is not uniform, while the hysteresis range in the FIG. 4 and FIG. 6 arrangements is constant. This variable hysteresis range does not raise any problem in the practical use if the resistance of the feedback resistor R6 is suitably selected. Although in the circuitry of FIG. 8 the resistance which corresponds to that of the resistor R3 in FIG. 4 is stepwisely changed, the resistance of the resistor R2 which is interposed between the power source +V and the second junction J2 may be changed instead by means of a like switch and a plurality of fixed resistors for obtaining like results.

Another embodiments will be described hereinbelow with reference to FIG. 10 and FIG. 11. These embodiments are basically the same as the embodiment of FIG. 4 except that the way of feedback for obtaining the hysteresis characteristic is different from that of FIG. 4.

Figure 10:
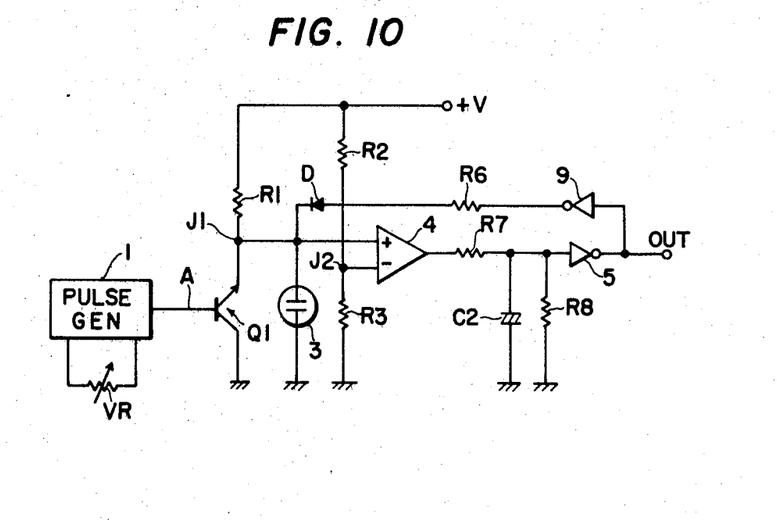
FIG. 10 is a schematic circuit diagram of another embodiment of the humidity sensing circuit in which the output signal of the circuitry is fed back in a different manner from that in FIG. 4.

In the circuitry of FIG. 10, a feedback circuit comprises an inverter 9, a resistor R6 and a diode D connected in series. Namely, although in the circuitry of FIG. 4, the feedback resistor R6 is interposed between the output terminal of the inverter 5 and the inverting input terminal of the comparator 4, the feedback circuit in FIG. 8 is interposed between the output terminal of the inverter 5 and the first junction J1. In detail, the output terminal of the inverter 5 is connected to an input terminal of the above mentioned inverter 9, the output terminal of which is connected via the resistor R6 to the anode of the diode D; and the cathode of the diode D is connected to the first junction J1. With this arrangement the charging current flowing into the humidity sensing element 3 is varied by a given amount compared with the charging current in the circuitry of FIG. 4 so that the range of the hysteresis characteristic with respect to the relative humidity can be maintained constant if the capacitance of the humidity sensing element 3 changes linearly with respect to the relative humidity.

Figure 11:
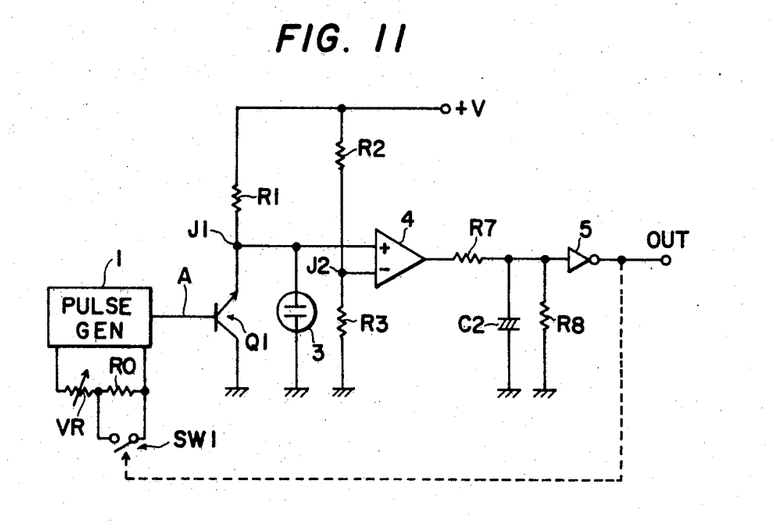
FIG. 11 is a schematic circuit diagram of another embodiment of the humidity sensing circuit in which the output signal of the circuitry is fed back in a different manner from those of FIG. 4 and FIG. 10.

In the circuitry of FIG. 11, a feedback circuit comprises a resistor R0 and a switching circuit SW1 connected in parallel with each other. The resistor R0 is connected in series with the variable resistor VR included in the pulse generator 1, and the switching circuit SW1 is controlled by the output signal of the inverter 5. With this provision the pulse width of the output pulse train signal of the pulse generator 1 is changed in response to the output pulse developed at the output terminal OUT so that a hysteresis characteristic is given to the circuitry of FIG. 11. The range of the hysteresis characteristic is constant in the same manner as in the circuitry of FIG. 4.

From the foregoing it will be understood that in accordance with the present invention the capacitance of the humidity sensing element 3 is readily measured by a circuit including a digital ICs, such as logic gate circuits and inverters inasmuch as no A.C. bridge circuit for measuring the impedance is employed. Therefore, there is no need to use a sinusoidal wave oscillator having high stability, and instead of such a sinusoidal wave oscillator a square wave oscillator can be used. Furthermore, the circuitry included in the apparatus according to the present invention is advantageous compared with the conventional circuitry since the accuracy of the humidity measurement is not influenced by the level of the output pulses from the oscillator at all. Furthermore, if the charging period for the humidity sensing element 3 varies due to the variation or fluctuation in the power source voltage, the reference voltage applied to the comparator 4 also changes in proportion to the amount of change in the charging period. Accordingly, the power source voltage variation hardly influences the accuracy of the humidity measurement.

The input impedance of the humidity sensing element 3 is low since the capacitante varies as the ambient relative humidity varies, in a relatively wide range, such as from 0.02 μF to 0.2 μF. Accordingly, the circuitry is hardly influenced by noises, and a resistor having a relatively low value, such 30 Kohms, may be used to provide a desired time constant together with the humidity sensing element 3. Therefore, a simple voltage comparator including two or three transistors, and thus having a relatively low input impedance, may be used as the voltage comparator 4. Namely, the circuitry may be simple in construction and low in cost, while the accuracy is well above the required practically level.

It will be understood, therefore, that the apparatus according to the present invention may be adapted to not only air-conditioning systems, such as a humidifer and/or a dehumidifier, but also to various devices and systems which may be or should be controlled in accordance with the sensed relative humidity. For instance, VTRs and copy machines, which should be deactivated when the humidity at a given position therein exceeds a predetermined humidity, may be controlled by sensing the humidity at the given position. It is obvious for those skilled in the art that many modifications and variations may be made without departing from the spirit of the present invention.

What is claimed is:

1. Apparatus for controlling humidity, including a humidity sensing circuit for producing an output signal indicative of the ambient humidity; and means for controlling the humidity in accordance with said output signal, said humidity sensing circuit comprising:
   (a) a humidity sensing element, the electrostatic capacitance of which varies in accordance with the ambient relative humidity;
   (b) a resistor connected in series with said humidity sensing element, said series circuit of said resistor and said humidity sensing element being connected to a D. C. power source so that said humidity sensing element is charged through said resistor;
   (c) a pulse generator for producing an output pulse train signal;
   (d) a switching circuit responsive to said pulse train signal for periodically discharging charge prestored in said humidity sensing element, ON/OFF operation of said switching circuit being controlled in accordance with the width of each pulse of said pulse train signal so that said switching circuit is periodically opened for a predetermined interval to exponentially charge said humidity sensing element in such a manner that a varying voltage derived from said D. C. source is developed across said humidity sensing element, the width and the duty cycle of said each pulse being selected such that said varying voltage across said humidity sensing element rises to a predetermined voltage when said electrostatic capacitance of said humidity sensing element assumes a given value; and
   (e) a voltage comparator responsive to the varying voltage across said humidity sensing element and to a reference voltage for producing an output signal which indicates that the humidity sensed has a predetermined relationship with respect to a reference humidity.

2. Apparatus for controlling humidity as claimed in claim 1, wherein said reference voltage is produced by a voltage divider interposed between said D. C. power source and ground.

3. Apparatus for controlling humidity as claimed in claim 1, wherein said switching circuit comprises a transistor the emitter-collector path of which is connected across said humidity sensing element.

4. Apparatus for controlling humidity as claimed in claim 1, wherein said pulse generator comprises means for adjusting the pulse width of said output pulse train signal.

5. Apparatus for controlling humidity as claimed in claim 4, wherein said means for adjusting the pulse width is a variable resistor.

6. Apparatus for controlling humidity as claimed in claim 1, wherein said means for controlling humidity comprises an SCR and a relay connected in series, the gate electrode of said SCR being responsive to the output signal of said voltage comparator.

7. Apparatus for controlling humidity as claimed in claim 6, further comprising a resistor interposed between said output terminal of said voltage comparator and said gate electrode, another resistor interposed between said gate electrode and ground, and a capacitor connected across the winding of said relay.

8. Apparatus for controlling humidity as claimed in claim 6 or 7, wherein said series circuit of said relay and said SCR is supplied with a half-wave or full-wave rectified voltage.

9. Apparatus for controlling humidity as claimed in claim 1, further comprising a voltage-hold circuit responsive to the output signal of said voltage comparator.

10. Apparatus for controlling humidity as claimed in claim 9, further comprising an inverter responsive to the output signal of said voltage-hold circuit, and a resistor interposed between the input terminal of said inverter and ground.

11. Apparatus for controlling humidity as claimed in claim 10, further comprising a feedback resistor interposed between the output terminal of said inverter and one of the input terminals of said voltage comparator.

12. Apparatus for controlling humidity as claimed in claim 10, further comprising a feedback circuit which includes a series circuit of a second inverter, a resistor and a diode, said feedback circuit being interposed between the output terminal of said first mentioned inverter and to said humidity sensing element.

13. Apparatus for controlling humidity as claimed in claim 10, wherein said pulse generator comprises a series circuit of a variable resistor and a fixed resistor for adjusting the pulse width, and a switching circuit connected across said fixed resistor, said switching circuit being responsive to the output signal of said inverter.

14. Apparatus for controlling humidity as claimed in claim 1, wherein said pulse generator comprises first, second and third inverters connected in series, a series circuit of a resistor and a capacitor connected between an input terminal of said first inverter and an output terminal of said second inverter, and a series circuit of a variable resistor and a fixed resistor connected between an output terminal of said first inverter and a junction connecting said resistor and capacitor which are connected in series.

15. Apparatus for controlling humidity as claimed in claim 2, wherein said voltage divider comprises a multi-contact switch and a plurality of fixed resistors respectively connected to the contacts of said multi-contact switch.

16. Apparatus for controlling humidity as claimed in claim 6, wherein said pulse generator is so constructed as to generate a pulse train signal having a frequency greater than four times the frequency of the voltage applied to said SCR.

17. A method of controlling humidity, comprising the steps of sensing ambient relative humidity by exposing to an environment to be humidity controlled a humidity sensing element, an electrostatic capacitance of which varies in accordance with ambient relative humidity, charging by a DC voltage the electrostatic capacitance of the humidity sensing element in accordance with a pulse train signal, the width and duty cycle of said pulse train signal being selected such that a varying voltage across the humidity sensing element derived from the DC source rises to a predetermined voltage when the electrostatic capacitance of the humidity sensing element assumes a given value, comparing the voltage across the humidity sensing element with a reference voltage to detect an interval required for charging the humidity sensing element so that the voltage across the humidity sensing element equals the reference voltage, changing the pulse width of the pulse train signal for setting a reference humidity and applying the signal developed by the humidity sensing circuit to a humidity control means.

18. A method of controlling humidity, comprising the steps of exposing to a region to be humidity controlled a humidity sensing element having an electrostatic capacitance that varies in accordance with ambient relative humidity, charging by a DC voltage the humidity sensing element and repeatedly discharging the element in accordance with a pulse train signal, the width and duty cycle of said pulse train signal being selected such that a varying voltage across the humidity sensing element derived from the DC source rises to a predetermined voltage when the electrostatic capacitance of the element assumes a given value, comparing the voltage across the humidity sensing element with a reference voltage to detect an interval required for charging the humidity sensing element so that the voltage across the humidity sensing element equals the reference voltage, changing the reference voltage for setting a reference humidity and applying a humidity sensing element electrostatic capacitance dependent output signal to a means for controlling ambient humidity.

* * * * *